United States Patent [19]

Winter et al.

[11] Patent Number: 5,254,760
[45] Date of Patent: Oct. 19, 1993

[54] INHIBITING POLYMERIZATION OF VINYL AROMATIC MONOMERS

[75] Inventors: Roland A. E. Winter, Armonk, N.Y.; Sheng-Shing Li, Danbury, Conn.; Leslie R. Gatechair, Katonah; Volker H. von Ahn, Mahopac, both of N.Y.

[73] Assignee: Ciba-Geigy Corporation, Ardsley, N.Y.

[21] Appl. No.: 921,824

[22] Filed: Jul. 29, 1992

[51] Int. Cl.$^5$ .................................. C07C 7/20
[52] U.S. Cl. .......................... 585/5; 585/3; 585/4
[58] Field of Search .................... 585/3, 4, 5

[56] References Cited

U.S. PATENT DOCUMENTS

| | | |
|---|---|---|
| 3,733,326 | 5/1973 | Murayama et al. |
| 3,988,212 | 10/1976 | Watson ............... 585/5 |
| 4,086,147 | 4/1978 | Watson |
| 4,105,506 | 8/1978 | Watson |
| 4,132,602 | 1/1979 | Watson |
| 4,132,603 | 1/1979 | Watson |
| 4,252,615 | 2/1981 | Watson |
| 4,341,600 | 7/1982 | Watson |
| 4,376,678 | 3/1983 | Partos ............... 585/4 |
| 4,466,904 | 8/1984 | Watson et al. |
| 4,468,343 | 8/1984 | Butler et al. |
| 4,654,451 | 3/1987 | Miller et al. |
| 4,967,027 | 10/1990 | Takahashi et al. |

FOREIGN PATENT DOCUMENTS

| | | | |
|---|---|---|---|
| 0240297 | 3/1987 | European Pat. Off. | |
| 1944233 | 4/1970 | Fed. Rep. of Germany | 585/4 |
| 3316745 | 6/1987 | Japan | 585/5 |
| 1-165534 | 6/1989 | Japan | |
| 1027150 | 7/1983 | U.S.S.R. | 585/5 |
| 1139722 | 2/1985 | U.S.S.R. | 585/4 |
| 1558888 | 4/1990 | U.S.S.R. | 585/4 |

OTHER PUBLICATIONS

Comprehensive Organic Chemistry, Sir Derek Barton, et al. (1979) pp. 205–214, Pergamon Press Oxford pp. 305–315.

Nitrones, nitronates & nitroxides Eli Breur et al. John Wiley & Sons, New York, 1989 pp. 313–329.

*Primary Examiner*—Asok Pal
*Attorney, Agent, or Firm*—Luther A. R. Hall

[57] ABSTRACT

The polymerization of a vinyl aromatic compound, such as styrene, during distillation or purification is very effectively inhibited by the presence of at least one stable nitroxyl compound together with at least one aromatic nitro compound.

23 Claims, No Drawings

INHIBITING POLYMERIZATION OF VINYL AROMATIC MONOMERS

The present invention pertains to a composition and a process for reducing premature polymerization of readily polymerizable vinyl aromatic compounds during monomer manufacturing processes.

BACKGROUND OF THE INVENTION

It is well-known that vinyl aromatic compounds, such as styrene, α-methylstyrene and other substituted vinyl benzenes, have a strong tendency to polymerize when subjected to elevated temperatures. Since vinyl aromatic compounds produced by common industrial methods contain by-products and impurities, these compounds must be subjected to separation and purification processes in order to be suitable for further industrial applications. Such separation and purification is generally accomplished by distillation techniques.

To prevent premature polymerization of vinyl aromatic monomers during the distillation purification process, various compounds have been used as polymerization inhibitors. Sulfur was widely employed in the past to inhibit polymerization of vinyl aromatic compounds. However in recent times, many chemical compounds have been disclosed or developed as substitutes for sulfur in polymerization inhibiting applications. These compounds have varying degrees of success for industrial use in the distillation process.

In a typical distillation process for a vinyl aromatic compound using a polymerization inhibitor, the mixture containing the vinyl aromatic compound to be distilled is generally contacted with the polymerization inhibitor before being subjected to distillation conditions in the distillation apparatus. It remains a significant problem still that the amount of polymer formed in the distillation system and in the high purity product recovered therefrom is substantially higher than desired. Still worse, occasionally, complete polymerization of the vinyl aromatic compound occurs in the distillation system causing considerable economic loss. A typical distillation system is described in detail in U.S. Pat. Nos. 4,252,615 and 4,341,600, the relevant parts of which are incorporated herein by reference.

U.S. Pat. No. 3,733,326 discloses the polymerization inhibition of vinyl monomers by free radical precursors. Soviet Patent No. 1,027,150 discloses the stabilization of styrene by using nitroxyl radical. Soviet Patent No. 1,139,722 discloses the use of a bis-nitroxyl radical as the thermal polymerization inhibitor for styrene. Japanese Hei 1-165534 discloses the use of 1-piperidyloxy derivatives as polymerization inhibitors for styrene. Soviet Patent No. 1,558,888 discloses the polymerization inhibition of styrene by a nitroxyl radical.

U.S. Pat. No. 4,086,147 discloses a process using 2-nitro-p-cresol as a polymerization inhibitor. U.S. Pat. Nos. 4,105,506 and 4,252,615 disclose a process using 2,6-dinitro-p-cresol as a polymerization inhibitor. U.S. Pat. Nos. 4,132,602 and 4,132,603 disclose the use of a halogenated aromatic nitro compound as a polymerization inhibitor for use during the distillation of vinyl aromatic compounds. However, these aromatic nitro compounds have relatively weak activity, and thus must be used at fairly high concentrations, especially at higher distillation temperatures. Considering the relatively high toxicity for human exposure, these aromatic nitro compounds cannot be regarded as acceptable agents for inhibiting polymerization.

In addition, U.S. Pat. Nos. 3,988,212 and 4,341,600 disclose the use of N-nitrosodiphenylamine combined with dinitro-cresol derivatives for inhibiting the polymerization of vinyl aromatic compounds under vacuum distillation conditions. U.S. Pat. No. 4,466,904 discloses the use of phenothiazine, 4-tert-butylcatechol and 2,6-dinitro-p-cresol as a polymerization inhibitor system in the presence of oxygen during heating of vinyl aromatic compounds. U.S. Pat. No. 4,468,343 discloses a composition and a process for utilizing 2,6-dinitro-p-cresol and either a phenylenediamine or 4-tert-butylcatechol in the presence of oxygen to prevent the polymerization of vinyl aromatic compounds during heating. European patent application 240,297 A1 teaches the use of a substituted hydroxylamine and a dinitrophenol to inhibit the polymerization of a vinyl aromatic compound at elevated temperatures in a distillation process. However, the effectiveness of said systems are oxygen dependent. This results in inconsistent inhibition due to an inconsistent distribution of air throughout the distillation column and raises the possibility of an increased explosion safety hazard. Accordingly, there exists a strong need for a stable polymerization inhibitor system which will effectively and safely prevent the polymerization of vinyl aromatic compounds during distillation and purification processes, particularly if air is absent.

OBJECTS OF THE INVENTION

One object of the present invention is to provide a composition comprising a vinyl aromatic compound and an effective inhibiting amount of a mixture of a stable hindered nitroxyl compound and an aromatic nitro compound to prevent premature polymerization during distillation or purification of said vinyl aromatic compound.

Another object of the instant invention is to provide a process for inhibiting the premature polymerization of a vinyl aromatic compound during distillation or purification which comprises incorporating therein an effective inhibiting amount of a mixture of a stable hindered nitroxyl compound and an aromatic nitro compound.

DETAILED DESCRIPTION

The instant invention pertains to a composition which comprises
  (a) a vinyl aromatic compound, and
  (b) an effective inhibiting amount, to prevent premature polymerization during distillation or purification of said vinyl aromatic compound, of a mixture of
    (i) 5 to 95% by weight, based on the total weight of components (i) and (ii), of a stable hindered nitroxyl compound, and
    (ii) 95 to 5% by weight, based on the total weight of components (i) and (ii), of an aromatic nitro compound.

The preferred amounts of components (i) and (ii) are 10 to 90% by weight of component (i) and 90 to 10% of component (ii); most preferably 20 to 80% by weight of component (i) and 80 to 20% by weight of component (ii).

The vinyl aromatic compounds of component (a) are selected from the group consisting of styrene, α-methylstyrene, vinyltoluene, divinylbenzene, styrenesulfonic acid and structural isomers, derivatives of said compounds and mixtures thereof. Preferably, component (a)

is styrene, α-methylstyrene, vinyltoluene or divinylbenzene; most preferably styrene.

The stable nitroxyl compounds useful in this invention have the generic structure

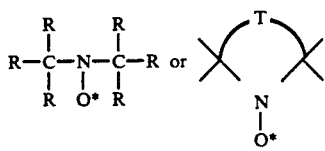

where each R is alkyl and T is a group required to complete a 5- or 6-membered ring.

Two or more nitroxyl groups may be present in the same molecule by being linked through the T moiety as exemplified below where E is a linking group.

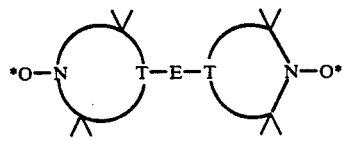

Preferably, the stable hindered nitroxyl compounds of component (i) are selected from the group consisting of
di-tert-butyl nitroxyl,
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl)adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine, and
4,4'-ethylenebis(1-oxyl-2,2,6,6-tetramethylpiperazin-3-one).

Most preferably, the compound of component (i) is bis(1-oxyl-2,2,6,6-tetramethylpiperidin-4-yl) sebacate, 2,4,6-tris-[N-butyl-N-(1-oxyl-2,2,6,6-tetramethylpiperidin-4-yl]-s-triazine, or 4,4'-ethylenebis(1-oxyl-2,2,6,6-tetramethylpiperazin-3-one).

Preferably, the aromatic nitro compound of component (ii) is selected from the group consisting of
1,3-dinitrobenzene
1,4-dinitrobenzene
2,6-dinitro-4-methylphenol
2-nitro-4-methylphenol
2,4-dinitro-1-naphthol,
2,4,6-trinitrophenol (picric acid)
2,4-dinitro-6-methylphenol
2,4-dinitrochlorobenzene
2,4-dinitrophenol
2,4-dinitro-6-sec-butylphenol
4-cyano-2-nitrophenol, and
3-iodo-4-cyano-5-nitrophenol.

Preferably the aromatic nitro compound contains a phenolic group as well as the nitro group.

Most preferably, the aromatic nitro compound is
2,6-dinitro-4-methylphenol,
2-nitro-4-methylphenol, or
2,4-dinitro-6-methylphenol.

The instant invention also pertains to a process for inhibiting the premature polymerization of a vinyl aromatic compound during distillation or purification which comprises
incorporating therein an effective inhibiting amount, to prevent premature polymerization during distillation or purification of said vinyl aromatic compound, of a mixture of
(i) 5 to 95% by weight, based on the total weight of components (i) and (ii), of a stable hindered nitroxyl compound, and
(ii) 95 to 5% by weight, based on the total weight of components (i) and (ii), of an aromatic nitro compound.

The aromatic vinyl monomer stabilization achieved by the instant invention in using a combination of a stable hindered nitroxyl compound (i) with an aromatic nitro compound (ii) is synergistic in nature, namely at the same total concentration of stabilizers greater monomer stabilization efficacy is achieved by using the combination of (i) and (ii) than by using either component (i) or (ii) alone.

The effective amount of polymerization inhibitors added may vary over a wide range depending upon the particular vinyl aromatic compound involved and the distillation and purification conditions. Preferably, the total amount of a nitroxyl radical and an aromatic nitro compound is from 1 ppm to about 2,000 ppm based upon the weight of the monomer being stabilized. For most vinyl aromatic compounds, the mixture of components (i) and (ii) is used in the range of 5 to 1,000 ppm. As the temperature increases, greater amounts of inhibitor are required. During distillation of the vinyl aromatic mixtures, the temperature of the reboiler is in the range of 50° C. to about 150° C. Since the boiling point of various members of the stable hindered nitroxyl compounds of component (i) and of the aromatic nitro compounds of component (ii) are different, compounds which have the desired boiling points can be easily selected. The compositions of this invention which inhibit the polymerization of the vinyl aromatic compound are also well suited for protecting the reboiler sections of a distillation column during distillation of vinyl aromatic monomers or the compressor sections before entering a distillation column.

The polymerization inhibitor composition can be introduced into the monomer to be protected by any conventional method. It may be added as a concentrated solution in suitable solvents just upstream of the point of desired application by any suitable means. In addition, the components (i) and (ii) may be injected separately into the distillation train along with the incoming feed, or through separate entry points providing there is an efficient distribution of the inhibitors. Since the inhibitors are gradually depleted during the distillation operation, it is generally necessary to maintain the appropiate amount of the inhibitor mixture in the distillation apparatus by adding inhibitors during the course of the distillation process. Such addition may be carried out either on a generally continuous basis or it may consist of intermittently charging inhibitor into the distillation system if the concentration of inhibitor is to be maintained above the minimum required level.

The instant invention enables the distillation and purification of vinyl aromatic compounds in manufacturing plants to operate more safely at an increased production rate compared to prior art processes because of its greater effectiveness with or without the presence of oxygen. This permits higher distillation temperatures with minimal polymer formation with accompanying economic and environmental advantages.

The following examples are presented for the purpose of illustration only and are not to be construed to limit the scope or nature of the instant invention in any manner whatsoever.

EXAMPLES 1-5

Commercial grade styrene is freed of tert-butylcatechol storage stabilizer by washing with 1N sodium hydroxide solution, water and a subsequent distillation under reduced pressure. A 300 mL 3-necked flask equipped with thermometer, condenser, rubber septum and magnetic stirrer bar is charged with 100 g of purified styrene and 20.0 mg of the test inhibitor or 20 mg of a test mixture of inhibitors to yield styrene with 200 ppm of total inhibitors. An oxygen-free atmosphere is established by five consecutive evacuations and backfilling with nitrogen, followed by sparging the styrene solution with pure nitrogen for 15 minutes. The vessel is then immersed into a mechanically stirred and thermostatically controlled oilbath at 120° C. and heated for 45 minutes. The amount of polystyrene formed is then determined by refractive index measurements, calibrated with authentic polystyrene in styrene solutions of known concentration. Without any added inhibitor, 6.20% by weight of polystyrene is formed. Polymer levels obtained with various inhibitors are listed in the table below. The blends of inhibitors are considerably more effective at reducing the amount of polymer formed than are either component by itself at the same total inhibitor concentration. There appears to be a synergistic effect on the polymerization inhibition by using both a stable hindered nitroxyl compound and an aromatic nitro compound together.

| Example No. | Inhibitors* | ppm | Percent Polymer (% by wt) | Relative Amount Polymer to Example 5 |
|---|---|---|---|---|
| Control | None | — | 6.20 | 10.67 |
| 1 | A | 200 | 1.42 | 2.45 |
|  | B | 0 |  |  |
| 2 | A plus | 150 | 0.25 | 0.43 |
|  | B | 50 |  |  |
| 3 | A plus | 100 | 0.33 | 0.57 |
|  | B | 100 |  |  |
| 4 | A plus | 50 | 0.33 | 0.57 |
|  | B | 150 |  |  |

| Example No. | Inhibitors* | ppm | Percent Polymer (% by wt) | Relative Amount Polymer to Example 5 |
|---|---|---|---|---|
| 5 | A | 0 |  |  |
|  | B | 200 | 0.58 | 1.00 |

*A is bis(1-oxyl-2,2,6,6-tetramethylpiperidin-4-yl) sebacate
B is 2,6-dinitro-4-methylphenol There is a clear synergistic inhibiting effect on the polymerization of styrene when a mixture of compounds A and B are used compared to either A or B alone at the same total concentration of inhibitor compound.

EXAMPLE 6

When the procedure of Example 3 is run in the presence of air, the polystyrene forms more slowly and the time needed to achieve the same percent polymer achieved in Example 3 (namely 0.33% by weight) is doubled from 45 minutes to 90 minutes.

EXAMPLES 7-9

The procedures of Examples 1,3 and 5 are repeated using only 10.0 mg of inhibitor or 10.0 mg of a mixture of inhibitors so that the total inhibitor concentration in styrene is 100 ppm. The results of these tests are given in the table below.

| Example No. | Inhibitors* | ppm | Percent Polymer (% by wt) | Relative Amount Polymer to Example 9 |
|---|---|---|---|---|
| Control | None | — | 6.20 | 7.46 |
| 7 | A | 100 | 3.08 | 3.71 |
|  | B | 0 |  |  |
| 8 | A plus | 50 | 0.50 | 0.60 |
|  | B | 50 |  |  |
| 9 | A | 0 |  |  |
|  | B | 100 | 0.83 | 1.00 |

*A is bis(1-oxyl-2,2,6,6-tetramethylpiperidin-4-yl) sebacate
B is 2,6-dinitro-4-methylphenol There is a clear synergistic inhibiting effect on the polymerization of styrene when a mixture of compounds A and B are used compared to either A or B alone at the same total concentration of inhibitor compound.

EXAMPLE 10

The procedure of Example 1 is repeated using 25 ppm of bis(1-oxyl-2,2,6,6-tetramethylpiperidin-4-yl) sebacate together with 25 ppm of 2,6-dinitro-4-methylphenol under a nitrogen atmosphere at 120° C. After 45 minutes of heating, the polystyrene content is only 1.64% by weight.

EXAMPLE 11

The procedure of Example 1 is repeated using 100 ppm of 1-oxyl-2,2,6,6-tetramethylpiperidin-4-yl benzoate together with 100 ppm of 1,3-dinitrobenzene at 120° C. under a nitrogen atmosphere. After heating for 45 minutes, the polystyrene content is only 2.20% by weight.

EXAMPLE 12

The procedure of Example 1 is repeated using 100 ppm of 2,4,6-tris-[N-butyl-N-(1-oxyl-2,2,6,6-tetramethylpiperidin-4-yl]-s-triazine together with 100 ppm of 4,6-dinitro-2-methylphenol at 120° C. under a nitrogen atmosphere. After heating for 45 minutes, the polystyrene content is only 0.16% by weight.

EXAMPLE 13

The procedure of Example 1 is repeated using 100 ppm of 4,4′-ethylenebis-(1-oxyl-2,2,6,6-tetramethylpiperazin-3-one) together with 100 ppm of 2,6-dinitro-4-methylphenol at 120° C. under a nitrogen atmosphere. After heating for 45 minutes, the polystyrene content is only 0.16% by weight.

EXAMPLE 14

The procedure of Example 1 is repeated using 100 ppm of 1-oxyl-2,2,6,6-tetramethylpiperidin-4-ol together with 100 ppm of 2-nitro-4-methylphenol at 120° C. under a nitrogen atmosphere. After heating for 45 minutes, the polystyrene content is only 0.49% by weight.

EXAMPLE 15

The procedure of Example 1 is repeated using 50 ppm of 1-oxyl-2,2,6,6-tetramethylpiperidin-4-one together with 50 ppm of 2,4-dinitrophenol at 120° C. under a nitrogen atmosphere. After heating for 45 minutes, the polystyrene content is only 0.5% by weight.

EXAMPLE 16

The procedure of Example 1 is repeated using 50 ppm of 1-oxyl-2,2,6,6-tetramethylpiperidine together with 50 ppm of 2,4,6-trinitrophenol (picric acid) at 120° C. under a nitrogen atmosphere. After heating for 45 minutes, the polystyrene content is 0.3% by weight.

EXAMPLE 17

When an effective inhibiting amount of a stable hindered nitroxyl compound together with an aromatic nitro compound are added to a styrene-containing feed stream in a continuous distillation unit, the formation of polystyrene in said unit is effectively minimized and inhibited.

What is claimed is:
1. A composition which comprises
   (a) a vinyl aromatic compound, and
   (b) an effective inhibiting amount, sufficient to prevent premature polymerization during distillation or purification of said vinyl aromatic compound, of a mixture of
      (i) 5 to 95% by weight, based on the total weight of components (i) and (ii), of a stable hindered nitroxyl compound, and
      (ii) 95 to 5% by weight, based on the total weight of components (i) and (ii), of an aromatic nitro compound.
2. A composition according to claim 1 wherein the amounts of components (i) and (ii) are 10 to 90% by weight of component (i) and 90 to 10% of component (ii).
3. A composition according to claim 2 wherein the amounts of components (i) and (ii) are 20 to 80% by weight of component (i) and 80 to 20% by weight of component (ii).
4. A composition according to claim 1 wherein the vinyl aromatic compound of component (a) is selected from the group consisting of styrene, α-methylstyrene, vinyltoluene, divinylbenzene, styrenesulfonic acid and structural isomers, derivatives of said compounds and mixtures thereof.

5. A composition according to claim 4 wherein the vinyl aromatic compound is styrene, α-methylstyrene, vinyltoluene or divinylbenzene.
6. A composition according to claim 5 wherein the vinyl aromatic compound is styrene.
7. A composition according to claim 1 wherein the stable hindered nitroxyl compound of component (i) is selected from the group consisting of
di-tert-butyl nitroxyl,
1-oxyl-2,2,6,6-tetramethylpiperidine,
1-oxyl-2,2,6,6-tetramethylpiperin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N′-bis(1-oxyl-2,2,6,6-tetramethylpiperidin-4-yl)adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine, and
4,4′-ethylenebis(1-oxyl-2,2,6,6-tetramethylpiperazin-3-one).
8. A composition according to claim 7 wherein the compound of component (i) is
bis(1-oxyl-2,2,6,6-tetramethylpiperidin-4-yl) sebacate,
2,4,6-tris-[N-butyl-N-(1-oxyl-2,2,6,6-tetramethylpiperidin-4-yl]-s-triazine, or
4,4′-ethylenebis(1-oxyl-2,2,6,6-tetramethylpiperazin-3-one).
9. A composition according to claim 1 wherein the aromatic nitro compound of component (ii) is selected from the group consisting of
1,3-dinitrobenzene
1,4-dinitrobenzene
2,6-dinitro-4-methylphenol
2-nitro-4-methylphenol
2,4-dinitro-1-naphthol,
2,4,6-trinitrophenol (picric acid)
2,4-dinitro-6-methylphenol
2,4-dinitrochlorobenzene
2,4-dinitrophenol
2,4-dinitro-6-sec-butylphenol
4-cyano-2-nitrophenol, and
3-iodo-4-cyano-5-nitrophenol.
10. A composition according to claim 9 wherein the compound of component (ii) is
2,6-dinitro-4-methylphenol,
2-nitro-4-methylphenol, or
2,4-dinitro-6-methylphenol.

11. A process for inhibiting the premature polymerization of a vinyl aromatic compound during distillation or purification which comprises
   incorporating therein an effective inhibiting amount, sufficient to prevent premature polymerization during distillation or purification of said vinyl aromatic compound, of a mixture of
   (i) 5 to 95% by weight, based on the total weight of components (i) and (ii), of a stable hindered nitroxyl compound, and
   (ii) 95 to 5% by weight, based on the total weight of components (i) and (ii), of an aromatic nitro compound.

12. A process according to claim 11 wherein the vinyl aromatic compound is distilled or purified at a temperature from 50° C. to 150° C.

13. A process according to claim 11 wherein the mixture of components (i) and (ii) is added to the vinyl aromatic compound continuously or intermittently upstream to the point where distillation or purification occurs.

14. A process according to claim 11 wherein the components (i) and (ii) are separately added at different entry points into the vinyl aromatic compound process stream prior to the point where distillation or purification occurs.

15. A process according to claim 11 wherein the amounts of components (i) and (ii) are 10 to 90% by weight of component (i) and 90 to 10% of component (ii).

16. A process according to claim 15 wherein the amounts of components (i) and (ii) are 20 to 80% by weight of component (i) and 80 to 20% by weight of component (ii).

17. A process according to claim 11 wherein the vinyl aromatic compound of component (a) is selected from the group consisting of styrene, α-methylstyrene, vinyltoluene, divinylbenzene, styrenesulfonic acid and structural isomers, derivatives of said compounds and mixtures thereof.

18. A process according to claim 17 wherein the vinyl aromatic compound is styrene, α-methylstyrene, vinyltoluene or divinylbenzene.

19. A process according to claim 18 wherein the vinyl aromatic compound is styrene.

20. A process according to claim 11 wherein the stable hindered nitroxyl compound of component (i) is selected from the group consisting of
di-tert-butyl nitroxyl,
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl)adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine, and
4,4'-ethylenebis(1-oxyl-2,2,6,6-tetramethylpiperazin-3-one).

21. A process according to claim 20 wherein the compound of component (i) is
bis(1-oxyl-2,2,6,6-tetramethylpiperidin-4-yl) sebacate,
2,4,6-tris-[N-butyl-N-(1-oxyl-2,2,6,6-tetramethylpiperidin-4-yl]-s-triazine, or
4,4'-ethylenebis(1-oxyl-2,2,6,6-tetramethylpiperazin-3-one).

22. A process according to claim 11 wherein the aromatic nitro compound of component (ii) is selected from the group consisting of
1,3-dinitrobenzene
1,4-dinitrobenzene
2,6-dinitro-4-methylphenol
2-nitro-4-methylphenol
2,4-dinitro-1-naphthol,
2,4,6-trinitrophenol (picric acid)
2,4-dinitro-6-methylphenol
2,4-dinitrochlorobenzene
2,4-dinitrophenol
2,4-dinitro-6-sec-butylphenol
4-cyano-2-nitrophenol, and
3-iodo-4-cyano-5-nitrophenol.

23. A process according to claim 22 wherein the compound of component (ii) is
2,6-dinitro-4-methylphenol,
2-nitro-4-methylphenol, or
2,4-dinitro-6-methylphenol.

* * * * *